(12) United States Patent
Kubara et al.

(10) Patent No.: US 11,632,490 B2
(45) Date of Patent: Apr. 18, 2023

(54) CAMERA MODULE, CAMERA, AND CABLE CONNECTION METHOD FOR CAMERA MODULE

(71) Applicant: PANASONIC I-PRO SENSING SOLUTIONS CO., LTD., Fukuoka (JP)

(72) Inventors: Takashi Kubara, Fukuoka (JP); Yosuke Kawauchi, Fukuoka (JP); Yuichi Hatase, Fukuoka (JP)

(73) Assignee: I-PRO CO., LTD., Tokyo (JP)

( * ) Notice: Subject to any disclaimer, the term of this patent is extended or adjusted under 35 U.S.C. 154(b) by 0 days.

(21) Appl. No.: 16/981,019

(22) PCT Filed: Apr. 4, 2019

(86) PCT No.: PCT/JP2019/015032
§ 371 (c)(1),
(2) Date: Sep. 15, 2020

(87) PCT Pub. No.: WO2019/194295
PCT Pub. Date: Oct. 10, 2019

(65) Prior Publication Data
US 2021/0021740 A1 Jan. 21, 2021

(30) Foreign Application Priority Data

Apr. 6, 2018 (JP) .............................. JP2018-074004

(51) Int. Cl.
*H04N 5/374* (2011.01)
*H04N 5/225* (2006.01)
(Continued)

(52) U.S. Cl.
CPC ......... *H04N 5/2253* (2013.01); *A61B 1/0011* (2013.01); *A61B 1/00114* (2013.01);
(Continued)

(58) Field of Classification Search
CPC .... H04N 5/2253; H04N 5/2254; H04N 7/183; H04N 2005/2255; H04N 5/225;
(Continued)

(56) References Cited

U.S. PATENT DOCUMENTS

| 4,831,456 A | 5/1989 | Takamura |
| 6,567,115 B1 | 5/2003 | Miyashita et al. |

(Continued)

FOREIGN PATENT DOCUMENTS

| EP | 3432571 | 1/2019 |
| JP | 63-272180 | 11/1988 |

(Continued)

OTHER PUBLICATIONS

Extended European Search Report from European Patent Office (EPO) in European Patent Appl. No. 19780649.0, dated Apr. 22, 2021.

(Continued)

*Primary Examiner* — Nguyen T Truong
(74) *Attorney, Agent, or Firm* — Greenblum & Bernstein, P.L.C.

(57) ABSTRACT

A camera module is provided with: an imaging element which is formed in a rectangular shape and has a plurality of pads provided to a back surface opposite from an imaging surface; a substrate where, on the same plane, a plurality of linear conductors are lined up in parallel and have an insulating coating in a rectangular shape such that the side of one end and the other end in the direction of extension of the conductors is shorter than one side of the imaging element, the conductors at the one end and the other end being exposed at a plate surface front and/or back; and a low-melting-point electroconductive material for connecting, to each of the pads, the conductors of the one end that (Continued)

are exposed due to one end surface of the substrate being abutted against the back surface.

18 Claims, 13 Drawing Sheets

(51) Int. Cl.
*A61B 1/00* (2006.01)
*A61B 1/05* (2006.01)
*H04N 7/18* (2006.01)

(52) U.S. Cl.
CPC ........... *A61B 1/051* (2013.01); *H04N 5/2254* (2013.01); *H04N 7/183* (2013.01); *H04N 2005/2255* (2013.01)

(58) Field of Classification Search
CPC ... A61B 1/0011; A61B 1/00114; A61B 1/051; A61B 1/00124; G02B 23/26; G02B 23/24; H01L 27/146
See application file for complete search history.

(56) References Cited

U.S. PATENT DOCUMENTS

| | | | |
|---|---|---|---|
| 2003/0111449 A1* | 6/2003 | Sinkunas | H05K 3/3494 219/121.85 |
| 2011/0034769 A1 | 2/2011 | Adair et al. | |
| 2011/0067231 A1* | 3/2011 | Kim | G01R 1/07342 29/739 |
| 2014/0302453 A1* | 10/2014 | Wany | A61B 1/00124 29/874 |
| 2015/0365571 A1 | 12/2015 | Wada et al. | |
| 2016/0072989 A1 | 3/2016 | Kennedy, II | |
| 2016/0205296 A1 | 7/2016 | Igarashi | |
| 2016/0216728 A1* | 7/2016 | Happoya | H01L 21/486 |
| 2017/0155860 A1* | 6/2017 | Ishizuka | G01R 1/07342 29/739 |
| 2018/0041671 A1* | 2/2018 | Fujimori | G01R 1/07342 29/739 |
| 2019/0021581 A1* | 1/2019 | Ishizuka | H05K 3/3405 |

FOREIGN PATENT DOCUMENTS

| | | |
|---|---|---|
| JP | 07-230872 | 8/1995 |
| JP | 2000-199863 | 7/2000 |
| JP | 2004-159970 | 6/2004 |
| JP | 2015-066300 | 4/2015 |
| JP | 2017-532100 | 11/2017 |

OTHER PUBLICATIONS

International Search Report (ISR) from International Searching Authority (Japan Patent Office) in International Pat. Appl. No. PCT/JP2019/015032, dated Jun. 18, 2019, along with an English language translation thereof.

Office Action from Japan Patent Office (JPO) in Japanese Patent Appl. No. 2020-512330, dated Nov. 15, 2022, together with an English language translation.

\* cited by examiner

CAMERA MODULE, CAMERA, AND CABLE CONNECTION METHOD FOR CAMERA MODULE

TECHNICAL FIELD

The present invention relates to a camera module, a camera, and a cable connection method of a camera module.

BACKGROUND ART

In general, in electronic endoscopes, an imaging device is installed inside and fixed to a metal shield pipe in a state that its positional relationship with an objective optical system is adjusted (i.e., focusing adjustments are made) correctly and a signal cable is joined, from behind, to terminals that are provided on the back surface of the imaging device (for example, refer to PTL 1). Core wires of the signal cable are joined to the respective terminals provided on the back surface of the imaging device by soldering. Further, joining portions between the core wires and the terminals are reinforced by forming a resin mold around them so as not to be broken during work of attaching the imaging device to the shield pipe inside it.

CITATION LIST

Patent Literature

[PTL 1] JP-A-2004-159970

SUMMARY OF INVENTION

Technical Problems

However, a very narrow electronic endoscope that is used being inserted in a very narrow pipe or hole such as a blood vessel may be configured in such a manner that the imaging device assumes a rectangular shape each side of which measures 1 mm or less. In this case, soldering the tips of the core wires of the signal cable to respective terminals (i.e., pads) that are provided on the back surface of the imaging device by manual work requires excellent skills and a large number of mounting steps. For example, fine processing of exposing portions of the core wires of the signal cable one by one is necessary. As such, the connection structure and connection method of connection between the imaging device and the signal cable of the conventional electronic endoscope have problems that automatic assembling is difficult in requiring human intervention of a worker having excellent skills and hence the manufacturing cost is high. For another thing, in very narrow cameras, there may occur case that it is desired to mount a bypass capacitor that is effective at noise reduction etc. between a power source and the ground. However, to meet that demand, it is necessary to newly add, among other things, a conversion board for mounting of the capacitor. In the above-mentioned conventional connection structure and connection method, manufacture is substantially impossible because of a further increase in the number of mounting steps.

The present disclosure has been conceived in view of the above circumstances in the at art and an object of the present invention is to provide a camera module, a camera, and a cable connection method of a cameral module capable of realizing mass production and reducing the manufacturing cost by making it possible to attain positioning between pads and conductors without requiring skills and to thereby enable automatic assembling easily.

Solution to Problems

The disclosure provides a camera module including an imaging device which is rectangular and is provided with plural pads on a back surface that is opposite to an imaging surface; a board which is shaped like a rectangular plate on which plural linear conductors are arranged and which is covered with an insulating coating, sides located at ends, in an extension direction of the conductors, of one end portion and the other end portion of the rectangular plate being shorter than each side of the imaging device, and the conductors being exposed in the one end portion and the other portion on at least one of a front plate surface and a back plate surface; and conductive materials which connect, to the pads, the exposed portions of the plural conductors in the one end portion, respectively, with one end surface of the board being in contact with the back surface.

Furthermore, the disclosure provides a camera including the camera module and a lens disposed on the side of the imaging surface of the imaging device.

Still further, the disclosure provides a cable connection method of a cameral module for connecting a cable to a camera module including an imaging device. The cable connection method includes a conductive material applying step of applying an unsolidified conductive material to at least one of a set of plural pads formed on a back surface, opposite to an imaging surface, of the imaging device, a set of plural linear pads which are exposed in one end portion and the other end portion of a plate-like board to be connected to the back surface of the imaging device, and a set of plural linear conductors which are exposed in one end portion and the other end portion of a plate-like board to be connected to the back surface of the imaging device; an end surface contact step of bringing one end surface of the board into contact with the back surface; a conductive material fixing step of electrically connecting the pads and the conductors via the conductive material that has been melted by blowing, over the conductive material, high-temperature air whose temperature is higher than a melting temperature of the conductive material; and a cable connecting step of joining plural core wires of the cable to portions, exposed in the other end portion, of the plural conductors, respectively.

The disclosure provides another cable connection method of a cameral module for connecting a cable to a camera module including an imaging device. The cable connection method includes a conductive material applying step of applying an unsolidified conductive material to at least one of a set of plural pads formed on a back surface, opposite to an imaging surface, of the imaging device and a set of plural linear conductors which are exposed in one end portion and the other end portion of a plate-like board to be connected the back surface of the imaging device; an end surface contact step of bringing one end surface of the board into contact with the back surface; a conductive material fixing step of electrically connecting the pads and the conductors via the conductive material that has been melted by applying laser light to the conductive material so that the temperature of the conductive material becomes higher than its melting temperature; and a cable connecting step of joining plural core wires of the cable to portions, exposed in the other end portion, of the plural conductors, respectively.

The disclosure provides a further cable connection method of a cameral module which is a method for connecting a cable to a camera module including an imaging device. The cable connection method includes a conductive material applying step of applying an unsolidified conductive material to at least one of a set of plural pads formed on a back surface, opposite to an imaging surface, of the imaging device and a set of plural linear conductors which are exposed in one end portion and the other end portion of a plate-like board to be connected to the back surface of the imaging device; an end surface contact step of bringing one end surface of the board into contact with the back surface; a conductive material fixing step of electrically connecting the pads and the conductors via the conductive material that has been melted by heating the conductive material in a reflow furnace; and a cable connecting step of joining plural core wires of the cable to portions, exposed in the other end portion, of the plural conductors, respectively.

Advantageous Effects of Invention

The disclosure can realize mass production and reduce the manufacturing cost by making it possible to attain positioning between pads and conductors without requiring skills and to thereby enable automatic assembling easily.

DESCRIPTION OF EMBODIMENTS

A camera module, a camera, and a cable connection method of a camera module according to a specific embodiment of the present disclosure will be hereinafter described in detail by referring to the accompanying drawings when necessary. However, unnecessarily detailed descriptions may be avoided. For example, detailed descriptions of well-known items and duplicated descriptions of constituent elements having substantially the same ones already described may be omitted. This is to prevent the following description from becoming unnecessarily redundant and thereby facilitate understanding of those skilled in the art. The following description and the accompanying drawings are provided to allow those skilled in the art to understand the disclosure thoroughly and are not intended to restrict the subject matter set forth in the claims.

Embodiment 1

First, an endoscope system 11 according to a first embodiment and a camera 100 (e.g., endoscope) that is part of the endoscope system 11 will be described.

Figure 1:
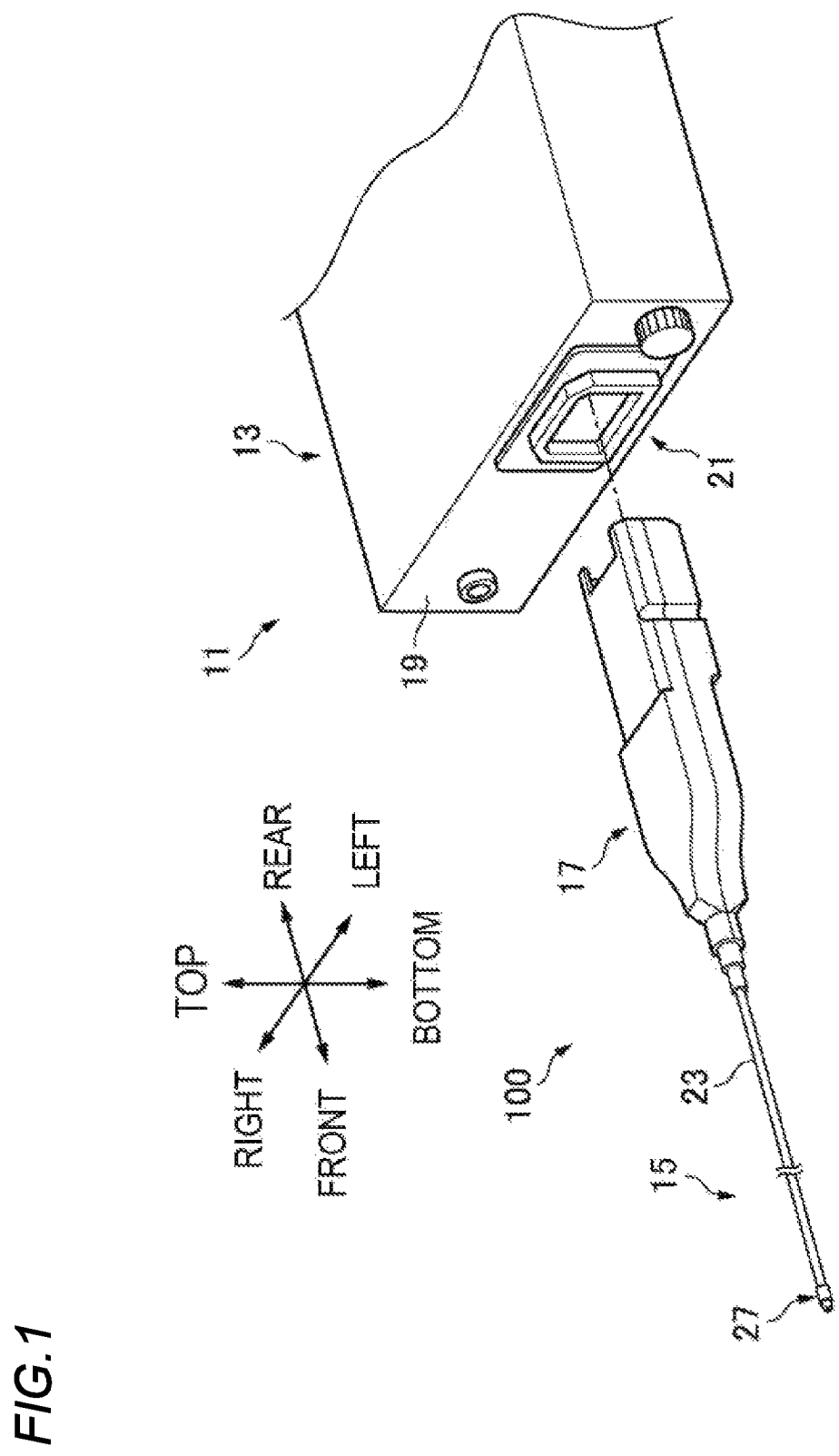
FIG. 1 is a perspective view showing an example appearance of an endoscope system according to a first embodiment.

FIG. 1 is a perspective view showing an example appearance of the endoscope system 11 according to a first embodiment. FIG. 1 is a perspective view showing the overall configuration of the endoscope system 11 which incorporates a camera 100 and a video processor 13. Directions that will be used in this specification will comply with directions shown in the drawings. The terms "top" and "bottom" correspond to the top and bottom of the video processor 13 which is set on a horizontal surface, respectively, and the terms "front" and "rear" correspond to the tip side of an insertion portion 15 of the camera 100 and the base side of a plug portion 17 (in other words, video processor side), respectively.

As shown in FIG. 1, the endoscope system 11 is configured so as to include the camera 100 which is, for example, a medical soft scope (e.g., endoscope) for medical purposes and the video processor 13 which performs known image processing etc. on a still image or a moving image taken by shooting the inside of an observation target (e.g., a human blood vessel). The camera 100 is equipped with the insertion portion 15 which extends approximately in the front-rear direction and is to be inserted into the inside of an observation target and the plug portion 17 to which a rear portion of the insertion portion 15 is connected.

The video processor 13 has a socket portion 21 which is open in its front wall 19. A rear portion of the plug portion 17 of the camera 100 is inserted in the socket portion 21. As a result, the camera 100 can transmits and receives power and various signals (video signal, control signal, etc.) to and from the video processor 13.

Power and various signals as mentioned above are guided by a cable 25 (see FIG. 3) inserted in a soft portion 23 to the soft portion 23 from the plug portion 17. Image data taken that is output from an imaging device 29 (see FIG. 3) provided in a tip portion 27 is transmitted to the video processor 13 via the cable 25 and the plug portion 17. The video processor 13 performs known image processing such as color correction and gradation correction on image data transmitted form the plug portion 17 and outputs image-processed image data to a display device (not shown). The display apparatus, which is a monitor apparatus having a display device such as a liquid crystal display panel, displays an image of a subject taken by the camera 100 (e.g., image data showing a situation in a blood vessel of a human body).

The insertion portion 15 has the flexible soft portion 23 whose rear end is connected to the plug portion 17 and the tip portion 27 which is connected to the tip of the soft portion 23. The soft portion 23 has a length that is suitable for methods of various endoscope examinations, endoscope surgeries, etc. The soft portion 23 is configured by, for example, covering the outer circumference of a metal thin plate wound spirally with a net and covering the outer circumference of the net with a covering so as to be made sufficiently flexible. The soft portion 23 connects the tip portion 27 and the plug portion 17.

Having a narrow diameter, the camera 100 can be inserted into a narrow body cavity. The term "narrow body cavity" is not limited to a blood vessel of a human body and include, for example, a ureter, a pancreatic duct, a bile duct, a bronchiole, etc. That is, it can be said that the camera 100 can be inserted into a blood vessel, a ureter, a pancreatic duct, a bile duct, a bronchiole, etc. of a human body. In other words, the camera 100 can be used for observation of a lesion in a blood vessel. The camera 100 is effective in deciding on an atherosclerotic plaque. The camera 100 can be used for endoscope observation in a heart catheter examination. Furthermore, the camera 100 is effective in detecting a blood clot and an atherosclerotic yellow plaque. In examining atherosclerotic lesions, color (white, light yellow, yellow) and a surface state (smooth, irregularity) are observed. In examining blood clots, a color (red, white, dark red, yellow, brown, mixed colors) is observed.

The camera 100 can also be used for diagnosis and treatment of renal pelvis/ureter cancer and sudden renal bleeding. In this case, the inside of a ureter and a renal pelvis by inserting the camera into the urethra and the urinary bladder and further into the ureter.

It is also possible to insert the camera 100 through the Vater papilla that opens in the duodenum. Bile is produced by the liver, passes through the bile duct, and is ejected through the Vater papilla of the duodenum and pancreatic juice is produced by the pancreas, passes through the pancreatic duct, and is ejected through the Vater papilla of the duodenum. The camera 100 enables observation of the bile duct or the pancreatic duct by inserting it through the Vater papilla which is the opening of the bile duct and the pancreatic duct.

Still further, the camera 100 can be inserted into the bronchi. The camera 100 is inserted into a subject body (i.e., person to be examined) in a supine posture through his or her oral cavity or nasal cavity. The camera 100 is inserted past the pharynx and larynx and then inserted into the trachea while allowing the user to visually recognize the vocal cords. The bronchus narrows every time it branches off. For example, a camera whose maximum diameter Dmax is smaller than 2 mm enables a check of lumens to the subsegmental bronchi.

Figure 2:
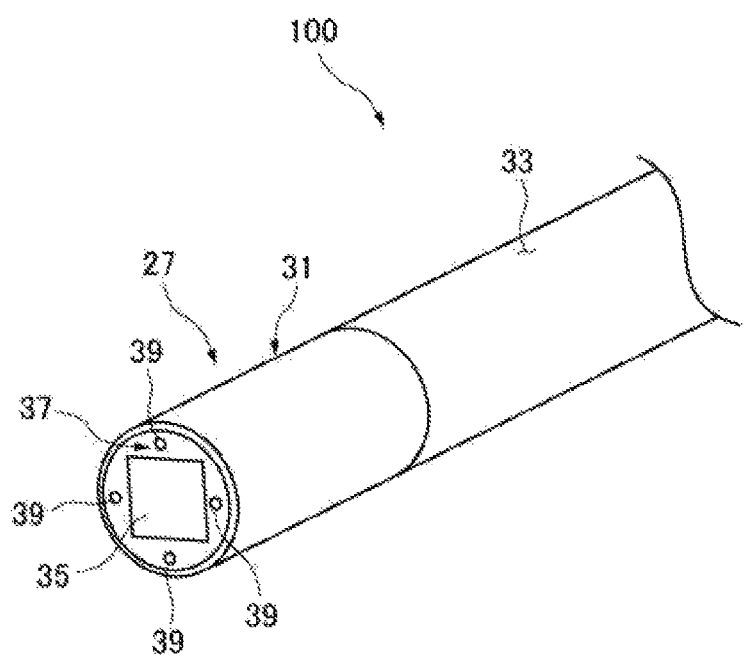
FIG. 2 is a perspective view showing an example appearance of a tip-side portion of a camera shown in FIG. 1.

FIG. 2 is a perspective view showing an example appearance of a tip-side portion of the camera 100 shown in FIG. 1. The camera 100 has a mold portion 31 in the tip portion 27. A tubular sheath 33 which has the same outer diameter as the tip portion 27 and covers at least part of the mold portion 31 is connected to the mold portion 31. The mold portion 31 is made of a mold resin and is molded in a column shape, and a lens and an imaging device (described later) are provided inside (partially buried in) the mold portion 31. The inner surface of the sheath 33 is fixed to the outer surface of a small diameter extension portion (not shown) extending from the rear end of the mold portion 31 with an adhesive or the like. The cable (described later) is inserted in the sheath 33.

The tip surface of the tip portion 27 is provided with a rectangular objective cover glass 35 at the center. Light exit end surfaces of four optical fibers 39 which constitute a light guide 37 are located outside the respective sides of the objective cover glass 35.

Figure 3:
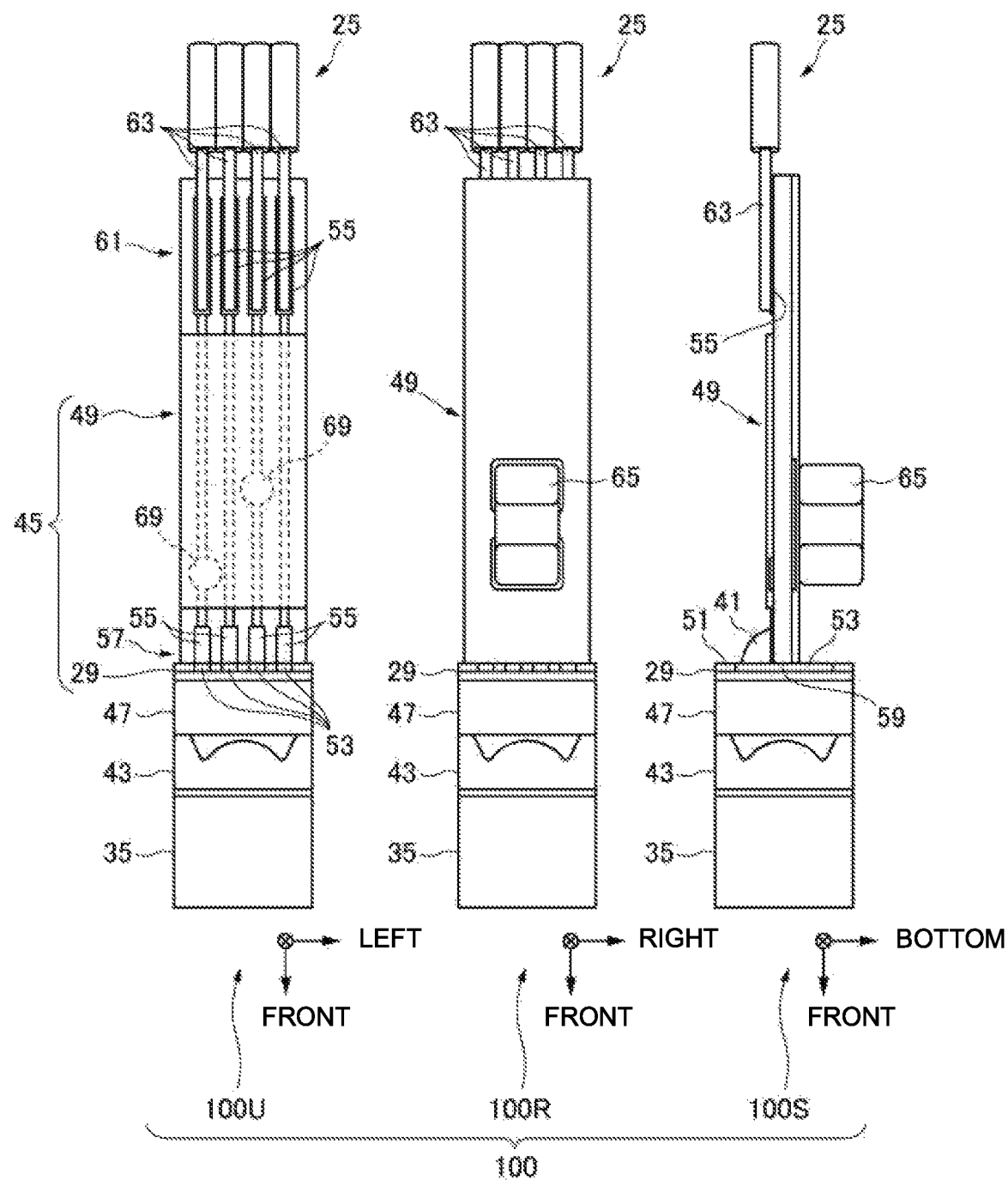
FIG. 3 is a plan view, a bottom view, and a side view of an essential part of the camera and illustrates its configuration.

FIG. 3 is a plan view, a bottom view, and a side view of an essential part of the camera 100 and shows its configuration. In FIG. 3, the plan view, the bottom view, and the side view of the camera 100 are denoted by 100U, 100R, and 100S, respectively. Low melting point conductive materials 41 (example conductive materials) are omitted in the plan view 100U.

The camera 100 has a lens 43 and a cameral module 45. The lens 43, which is a single lens, is disposed in the rear of the objective cover glass 35 which is disposed closest to the objective side in the tip portion 27. The imaging device 29 is disposed in the rear of the lens 43 with a device cover glass 47 interposed between the lens 43 and the imaging device 29. A board 49 is connected to the imaging device 29. The imaging device 29 and the board 49 constitute a cameral module 45. The cable 25 which used for transmitting image data taken by the imaging device 29 is connected to the cameral module 45 from behind. The objective cover glass 35, the lens 43, the device cover glass 47, the board 49, and part of the cable 25 are provided inside (partially buried in) the mold portion 31.

The imaging device 29 has a rectangular (e.g., square) shape each side of which measures 1 mm or less (e.g., about 0.5 to 1 mm). The imaging device 29 is provided with plural pads on its back surface 51 opposite to its imaging surface.

Figure 4:
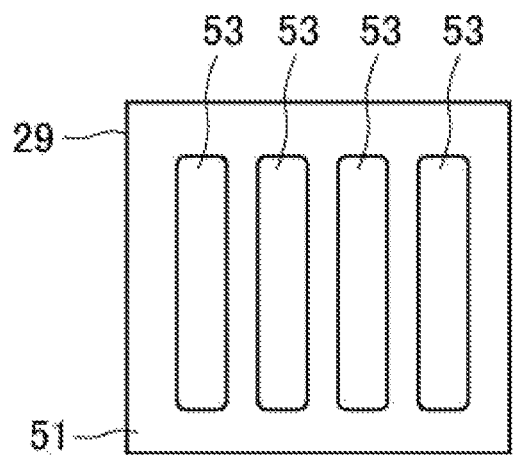
FIG. 4 is a rear view of an imaging device in which pads are formed so as to be approximately the same in length as each side of the imaging device.

FIG. 4 is a rear view of the imaging device 29 in which the pads 53 are formed so as to be approximately the same in length as each side of the imaging device 29. Plural (four in the example shown in FIG. 4) pads 53 having a rectangular shape the longer side of which is a little shorter than each side of the back surface 51 can be arranged at regular intervals in the direction perpendicular to their longer sides on the approximately square back surface 51 of the imaging device 29. Each pad 53 is used for circuit connection for power, an image signal, GND (grounding), CLK (e.g., input of a clock and a command from the video processor 13), or the like.

Figure 5:
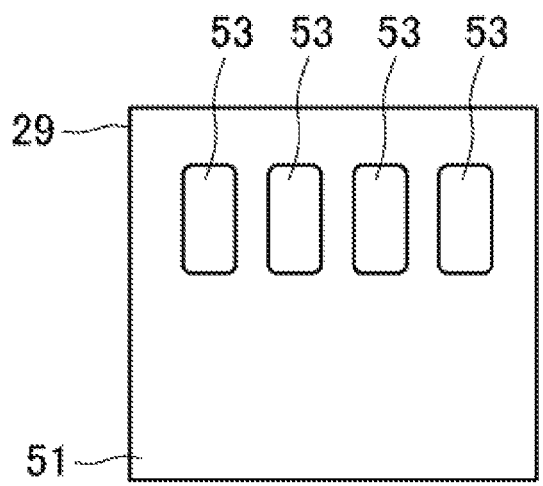
FIG. 5 is a rear view of an imaging device in which pads are formed so as to measure approximately half of each side of the imaging device in length.

FIG. 5 is a rear view of an imaging device 29 in which the pads 53 are formed so as to measure approximately half of each side of the imaging device 29 in length. As shown in FIG. 5, plural (four in the example shown in FIG. 5) pads 53 having a rectangular shape the longer side of which is a little shorter than half of each side of the back surface 51 can be arranged at regular intervals in the direction perpendicular to their longer sides on the approximately square back surface 51 of the imaging device 29. In this case, the plural pads 53 are located close to one side of the back surface 51 in a region that measures approximately half of the back surface 51 in area.

Figure 6:
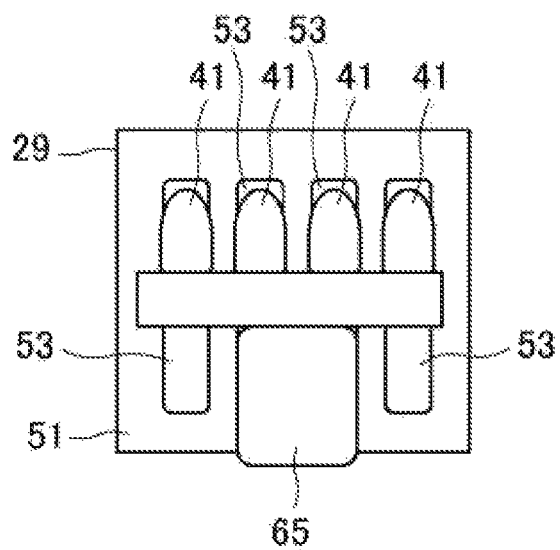
FIG. 6 is a rear view of the imaging device to whose pads shown in FIG. 4 a board is fixed.

FIG. 6 is a rear view of the imaging device 29 to whose pads 53 shown in FIG. 4 the board 49 is fixed. The end surface 59 (see FIG. 3) of one end portion 57, in the extension direction of conductors 55, of the board 49 is in contact with the back surface 51 of the imaging device 29. Portions, exposed in the one end portion 57 of the board 49, of the conductors 55 are fixed to the pads 53 formed on the back surface 51 of the imaging device 29 by the low melting point conductive materials 41 (example conductive materials), respectively. That is, the conductors 55 are electrically connected to the pads 53 by the low melting point conductive materials 41, respectively. The board 49 may be formed with lands in regions where conductors 55 are exposed, respectively. The pads 53 shown in FIG. 6 extend downward to below the board 49. In the first embodiment, the bottom surface of the board 49 has no exposed portions. Low melting point conductive materials 41 may be fixed to the respective pads 53 which extend downward to below the board 49. The one end portion 57 of the board 49 may be sandwiched between front portions and back portions of the low melting point conductive materials 41 fixed to the respective pads 53. This makes it possible to increase the strength of fixing of the imaging device 29 and the board 49.

Figure 7:
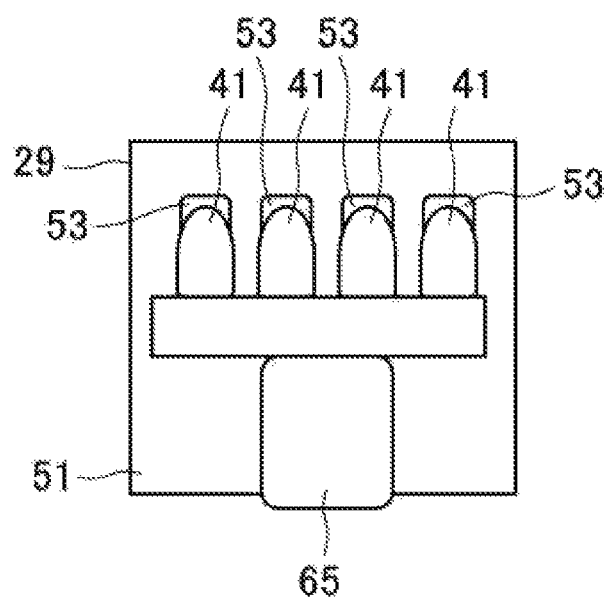
FIG. 7 is a rear view of the imaging device to whose pads shown in FIG. 5 the board is fixed.

FIG. 7 is a rear view of the imaging device 29 to whose pads 53 shown in FIG. 5 the board 49 is fixed. As shown in FIG. 7, the pads 53 may be formed so as to have a small area that enables joining to portions, exposed in the one end portion 57, of the board 49. This makes it possible to suppress thermal stress on the imaging device 29 when the low melting point conductive materials 41 melt.

For example, the low melting point conductive material 41 may be cream solder formed by kneading solder powder into paste-like flux. The use of cream powder makes it possible to transfer fine patterns onto the pads 53 or the conductors 55 by a printing machine.

Figure 8:
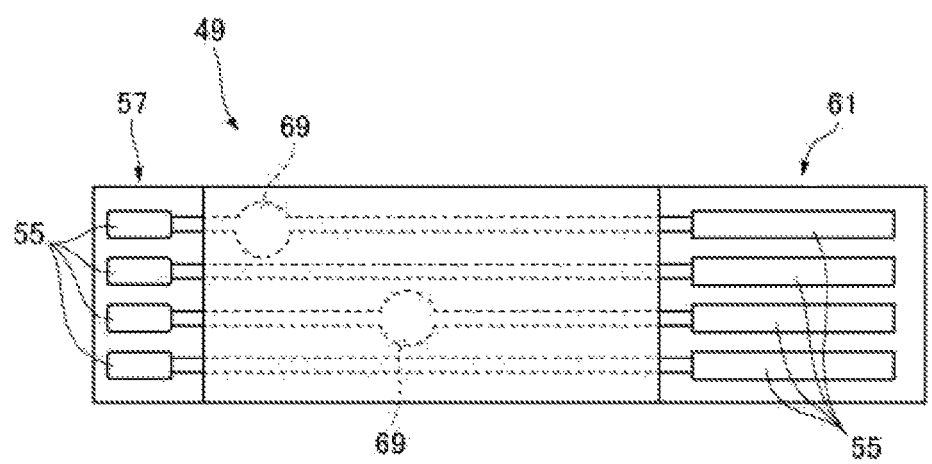
FIG. 8 is a plan view of the board shown in FIG. 3.

FIG. 8 is a plan view of the board 49 shown in FIG. 3. The board 49 is shaped like a plate on which plural (e.g., four in the embodiment) linear conductors are arranged parallel with each other in the same plane and are covered with an insulating coating. The board 49 has a rectangular shape in which the sides, located at the ends in the extension direction of the conductors 55, of the one end portion 57 and the other end portion 61 are shorter than each side of the imaging device 29. The portions, in the one end portion 57 and the other end portion 61 of the board 49, of the conductors 55 are exposed on at least one of the front surface and the back surface of the board 49. In the first embodiment, portions, in the one end portion 57 and the other end portion 61, of the conductors 55 are exposed on only the top plate surface.

The board 49 may be a flexible FFC (flexible flat cable), for example.

The structure of the board 49 is not limited to the structure that the conductors 55 are covered with an insulating coating and may be such that the conductors 55 are printed on an insulating substrate. Examples of such a board 49 are an FPC (flexible printed wiring board) in which the conductors 55 are pattern-printed on a flexible insulating substrate and a laminate board in which the conductors 55 are pattern-printed on an insulating substrate. In this case, portions of the conductors 55 other than the portions connected to the pads 53 or the core wires 63 be covered with an insulating layer.

The exposed portions of the conductors 55 can be formed by preventing the conductors 55 from being covered with the insulating coating by masking those portions in advance on at least one of the front surface and the back plate surface. Alternatively, the exposed portions of the conductors 55 may be formed by removing the insulating coating there on at least one of the front surface and the back plate surface. In either case, insulating coating layers are interposed between the conductors 55.

Figure 9:
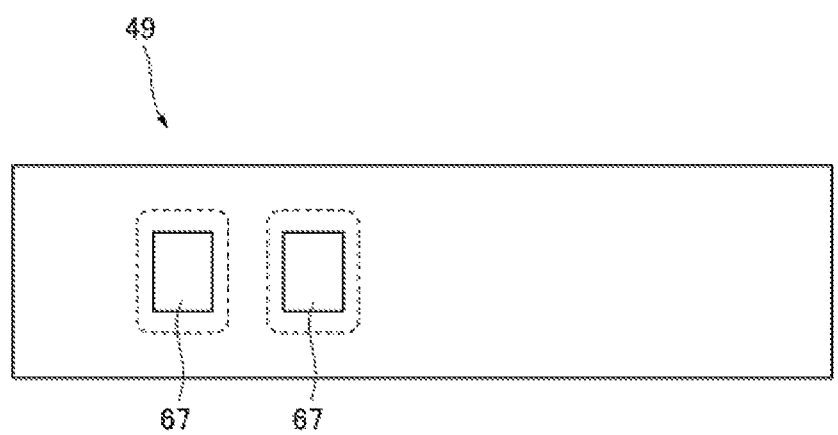
FIG. 9 is a bottom view of the board shown in FIG. 8.

FIG. 9 is a bottom view of the board 49 shown in FIG. 8. In the camera module 45, an electric component 65 (see FIG. 3) that is electrically connected to conductors 55 is mounted on the board 49. An example of the electric component 65 is a bypass capacitor that is effective at noise reduction etc. The board 49 is formed with lands 67 for mounting of the electric component 65. In the first embodiment, the lands 67 are formed on the bottom surface of the board 49. The lands 67 are connected to conductors 55 formed on the front surface of the board 49 through via holes 69, respectively.

As shown in FIG. 3, in the camera module 45, the plural core wires 63 of the cable are connected to the portions, exposed in the other end portion 61 of the board 49, of the conductors 55, respectively. In the first embodiment, the cable 25 is a ribbon-shaped cable in which the plural core wires 63 are arranged in the same plane and covered with an insulating covering together.

In the cable 25, the core wires 63 are covered with respective internal coverings. The plural core wires 63 which are covered with respective internal coverings are covered with a shield covering together outside the internal coverings.

Next, a cable connection method of the camera module 45 according to the first embodiment will be described with reference to FIG. 10.

Figure 10:
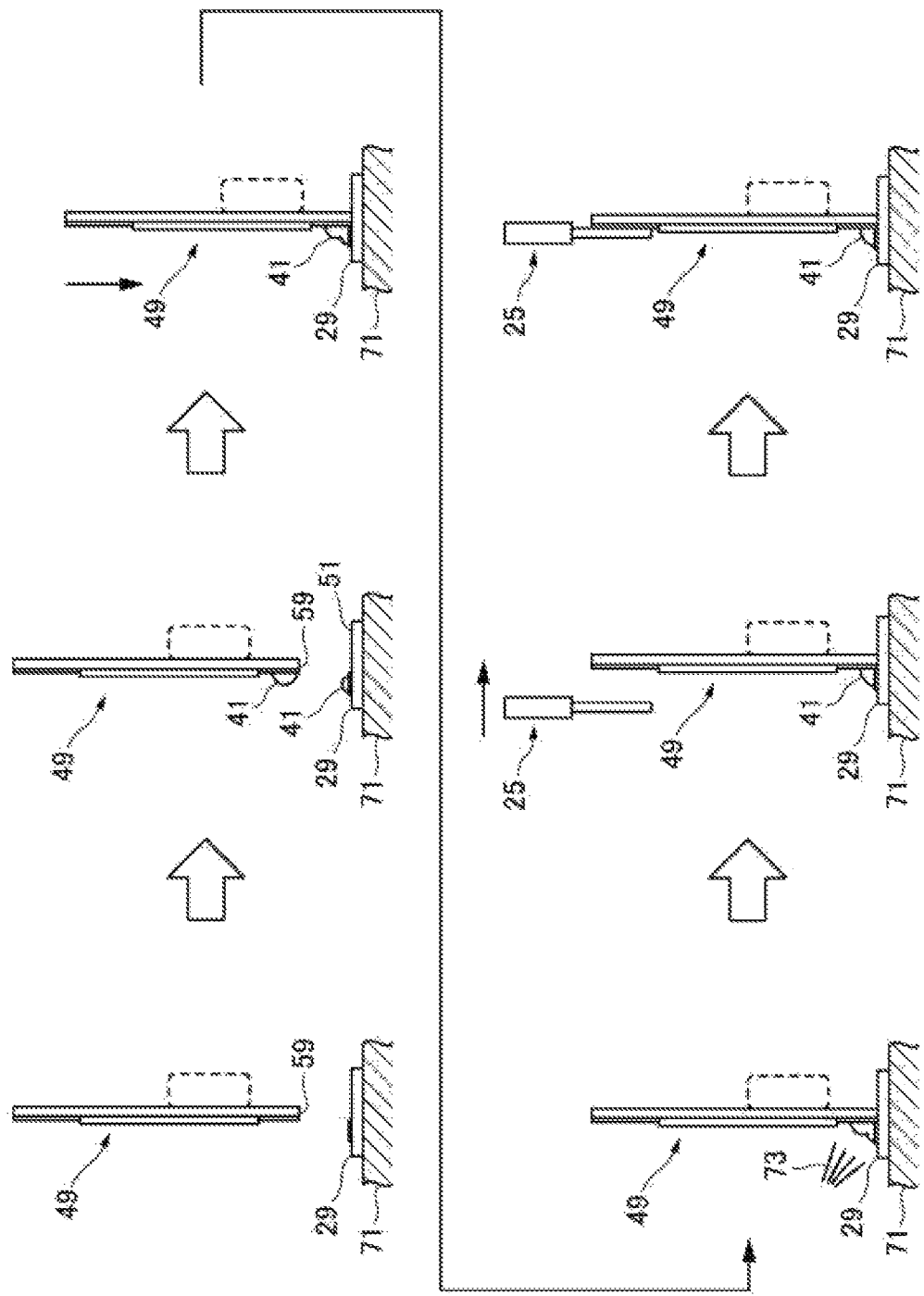
FIG. 10 is a process diagram illustrating an example procedure of a cable connection method of a cameral module.

FIG. 10 is a process diagram illustrating an example procedure of the cable connection method of the camera module 45.

In the cable connection method of the camera module 45, the imaging device 29 is arranged on a surface plate 71 or the like having a horizontal top surface. For example, the imaging device 29 is put with its back surface 51 up. The low melting point conductive materials 41 have been applied to the pads 53 of the imaging device 29 and the conductors 55 of the board 49 in advance in a conductive material applying step.

The one end surface 59 of the board 49 to which the low melting point conductive materials 41 are applied is brought into contact with the back surface 51 of the imaging device 29 in an end surface contact step. Since the one end surface 59 of the board 49 abuts on the back surface 51, the low melting point conductive materials 41 applied to the pads 53 come close to or come into contact with those applied to the conductors 55, respectively.

Subsequently, in a conductive material fixing step, high-temperature air 73 whose temperature is higher than the melting temperature of the low melting point conductive materials 41 is blown over the low melting point conductive materials 41. After the low melting point conductive materials 41 have been melted, they are solidified by room temperature cooling. As a result, the pads 53 on the imaging device 29 are electrically connected to the respective conductors 55 by the low melting point conductive materials 41 that are solidified after being melted.

Finally, in a cable connection step, the plural core wires 63 of the cable 25 are joined to the portions, exposed in the other end portion 61 of the board 49, of the conductors 55, respectively. The cable connection of the camera module 45 is thus finished.

Further, as for the cable connection method of the camera module, an alternative conductive material fixing step is possible in which laser light is applied to the low melting point conductive materials 41 so that its temperature becomes higher than its melting temperature and the pads 53 are thereby connected to the respective conductors 55 electrically via the melted low melting point conductive materials 41.

As for the cable connection method of the camera module, a further alternative conductive material fixing step is possible in which the pads 53 are electrically connected to the respective conductors 55 via the low melting point conductive materials 41 that have been melted by being heated in a reflow furnace.

The electric component 65 may be mounted on the board 49 at any of various kinds of timing, that is, before, after, and at the same time as the joining of the imaging device 29 and the board 49. The board 49 and the cable 25 may be jointed to each other at any of various kinds of timing, that is, before, after, and at the same time as the joining of the imaging device 29 and the board 49.

Next, the workings of the above-configured camera 100 according to the first embodiment will be described.

The cameral module 45 according to the first embodiment is equipped with the imaging device 29 which has a rectangular shape each side of which measures, for example, 1 mm or less and whose back surface 51 opposite to its imaging surface is provided with the plural pads 53. The cameral module 45 is equipped with the board 49 which is shaped like a rectangular plate that is covered with an insulating coating. Sides, located at ends in the extension direction of the conductors 55, of the one end portion 57 and the other end portion 61 of the rectangular plate are shorter than each side of the imaging device 29. The plural linear conductors 55 are arranged parallel with each other in the same plane and exposed in the one end portion 57 and the other portion 61 on at least one of the front plate surface and the back plate surface. The cameral module 45 has the low melting point conductive materials 41 which connect, to the pads 53, the exposed portions of the plural conductors 55 in the one end portion, respectively, with the one end surface 59 of the board 49 being in contact with the back surface 51.

As described above, in the cameral module 45 according to the first embodiment, the plural pads 53 are formed on the back surface 51 of the imaging device 29. The one end surface 59 of the one end portion 57 of the board 49 is in contact the back surface 51 of the imaging device 29. In the board 49, each insulating coating layer is interposed between conductors. Thus, the end surfaces of the conductors 55 and the end surfaces of the insulating coating layers exist in the same plane in the one end surface 59 of the board 49. As such, the one end portion 57 of the board 49 is shaped like a plate that has a flat end surface having a composite structure that includes the surfaces of the plural conductors 55 and the insulating coating layers interposed between the conductors 55.

It is preferable that the one end surface 59 of the board 49 be perpendicular to the front surface and the back surface of the plate. This makes it possible to bring the one end surface 59 into contact with the back surface 51 of the imaging device 29 from the direction perpendicular to it in positioning the board 49 with respect to the back surface 51. Since the one end surface 59 of the board 49 is opposed to the back surface 51 parallel with it, a slip is not prone to occur when the board 49 is brought into contact with the back surface 51. In other words, the board 49 can be positioned with respect to the imaging device 29 easily.

Since the board 49 is shaped like a plate, it can be chucked more easily in the thickness direction than one very thin core wire though it is a minute component. As such, the board 49 can be positioned with respect to the pads 53 of the imaging device 29 easily with high precision. As a result, the board 49 can be positioned easily by automatic assembling.

The plate-like one end portion 57 of the board 49 assumes a rectangle whose sides are shorter than each side (e.g., 1 mm) of the imaging device 29. As described above, the one end portion 57 has the composite structure in which each insulating coating layer is interposed between conductors.

The buckling load of the one end portion 57 can be made larger than that of a conventional one very thin core wire having the same diameter. This makes it possible to position the board 49 with higher accuracy while making its deformation smaller than in a case that a conventional very thin core wire is brazed by bringing it into contact with a pad 53 in the axial line direction. As a result, the yield of a brazing step of automatic assembling can be increased.

In the imaging device 29 and the board 49 in which the one end surface 59 is in contact with the back surface 51, the conductors 55 are in contact with or are located close to the respective pads 53 perpendicularly to them. That is, the pads 53 and the conductors 55 constitute perpendicular corner structures. The low melting point conductive materials 41 are solidified in the respective corner structures. The conductors 55 are electrically connected to and fixed to the pads 53 by the low melting point conductive materials 41 that are solidified being in close contact with the conductors 55 and the pads 53, respectively. As such, the low melting point conductive materials 41 can fix the board 49 to the imaging device 29 in addition to establishing electrical continuity between the conductors 55 and the pads 53.

In the board 49, the angles formed by the one end surface 59 and the front and back surfaces are not limited to 90°. By setting the angles formed by the one end surface 59 and the front and back surfaces of the board 49 different from 90°, the shooting direction of the imaging device 29 and the board 49 extending in the horizontal direction can form an elevation angle or a dip angle. The structure that the imaging device 29 is inclined with respect to the board 49 in this manner can be employed suitably in, for example, an oblique-viewing endoscope in which the observation direction is inclined with respect to the insertion direction.

As such, the cameral module 45 according to the first embodiment can realize mass production and reduce the manufacturing cost by making it possible to attain positioning between the pads 53 and the conductors 55 without requiring skills and to thereby enable automatic assembling easily.

In the camera module 45, the plural core wires 63 of the cable 25 are connected to portions, exposed in the other end portion 61 of the board 49, of the plural conductors 55, respectively.

In this cameral module 45, the core wires 63 of the cable 25 are connected to portions, exposed in the other end portion 61 of the board 49, of the plural conductors 55, respectively. In the board 49 which assumes a rectangle, the sides, to be brought into contact with the back surface 51 of the imaging device 29, of the one end portion 57 are shorter than each side (e.g., 1 mm or less) of the imaging device 29. On the other hand, the pair of parallel side edges, perpendicular to each of the above sides of the one end portion 57, of the board 49 are free of the restriction that they should be shorter than each side of the imaging device 29. That is, the side edges of the board 49 can be longer than each side of the imaging device 29. As a result, in the board 49, longer portions of the conductors 55 can be exposed in the other portion 61 than in the one end portion 57. In the other portion 61 of the board 49, the parallel core wires 63 of the cable 25 can easily be brazed to long exposed portions, extending in the longitudinal direction, of the linear conductors 55.

In the camera module 45, the plural core wires 63 each of which is insulated being covered with an internal covering of the cable 25 are covered with a shield covering together outside the internal coverings.

In this camera module 45, crosstalk occurring in the core wires 63 of the cable 25 can be suppressed. For example, the camera 100 which employs the camera module 45 as a constituent member may be used being inserted into a treatment tool insertion channel (e.g., forceps tube) of an endoscope. In this case, the shield covering that covers the cable 25 which is connected to the camera 100 can effectively suppress crosstalk with, for example, an image signal wire that is connected to the endoscope-side imaging device.

In the camera module 45, the electric component 65 is mounted on the board 49 so as to be electrically connected to conductors 55.

In this camera module 45, in the case where the electric component 65 (e.g., bypass capacitor) which is effective at noise reduction etc. is incorporated, the electric component 65 can be mounted on the board 49 directly without the need for adding a new conversion board for incorporation of the capacitor. Thus, the electric component 65 can be incorporated without requiring an additional component.

The camera 100 according to the first embodiment is equipped with the camera module 45 and the lens 43.

Configured in this manner, the camera 100 according to the first embodiment, an image of light coming from a part being shot is formed on the light receiving surface of the imaging device 29 of the camera module 45 by the lens 43. The imaging device 29 converts the image forming light into an electrical signal and outputs, as an image signal, the electrical signal to the cable 25 via the board 49 which is a component of the cameral module 45. In the camera 100, the cable 25 can be connected to the imaging device 29 which is a minute component easily with high accuracy by virtue of the intervention of the board 49. This enables mass production of the camera 100 by automatic assembling.

One cable connection method of a camera module includes a conductive material applying step of applying an unsolidified conductive material 41 to at least one of a set of plural pads 53 formed on the back surface 51, opposite to the imaging surface, of the imaging device 29 shaped like a rectangle each side of which measures 1 mm or less and a set of plural linear conductors 55 which are exposed in the one end portion 57 and the other end portion 61 of the plate-like board 49 to be connected to the back surface 51 of the imaging device 29; an end surface contact step of bringing the one end surface 59 of the board 49 into contact with the back surface 51; a conductive material fixing step of electrically connecting the pads 53 and the conductors 55 via the low melting point conductive material 41 that has been melted by blowing, over the low melting point conductive material 41, high-temperature air whose temperature is higher than a melting temperature of the low melting point conductive material 41; and a cable connecting step of joining the plural core wires 63 of the cable 25 to portions, exposed in the other end portion 61, of the plural conductors 55, respectively.

In this cable connection method of a camera module according to the first embodiment, cream solder is applied to the pads 53 and the conductor 55 in the conductive material applying step. With the pads 53 and the conductor 55 coated with the cream solder, the one end surface 59 of the board 49 is brought into contact with the back surface 51 of the imaging device 29 in the end surface contact step. In this manner, the positioning between the plural conductors 55 and the plural respective pads 53 is performed easily with high accuracy at one time. With the pads 53 and the conductor 55 kept in this positioned state, the cream solder is melted by blowing high-temperature air over it in the conductive material fixing step. The melted cream solder comes to be fixed to the pads 53 and the conductor 55. Whereas the one end portion 57 of the board 49 is connected to the imaging device 29, the conductors 55 are exposed in the other portion 61 in large areas. As a result, the core wires 63 of the cable 25 can easily be brazed to portions, located in the other portion 61 of the board 49, of the conductors 55 because the core wires 63 and the conductors 55 are parallel with in their extension direction.

Furthermore, in this cable connection method of a camera module, the positioning between the conductors 55 (minute components) and the respective pads 53 (minute components) can performed easily with high accuracy at the same time by bringing the one end surface 59 of the board 49 bearing the plural conductors 55 that are exposed in the one end portion 57 into contact with the back surface 51 of the imaging device 29. The linear conductors 55 can be exposed on the board 49 connected to the imaging device 29 in large areas in their extension direction. Furthermore, the core wires 63 can be brazed to the respective linear conductors 55 in a state that core wires 63 extend parallel with the conductors 55. As a result, in this cable connection method of a camera module, the cable 25 can be connected more easily than in a conventional method in which the tips of the core wires 63 are directly brazed to the plural respective pads 53 of the imaging device 29 in their axial line directions. That is, in this cable connection method of a camera module, the intervention of the board 49 allows work of brazing the conductors 55 (minute components) to the pads 53 (minute components), which is very difficult to perform manually in the art, to be performed with sufficient margins in time and technique, whereby the cable 25 can be connected to the imaging device 29 easily. Such ease of positioning makes it possible to realize automatic assembling easily.

Another cable connection method of a camera module includes a conductive material applying step of applying an unsolidified conductive material 41 to at least one of a set of plural pads 53 formed on the back surface 51, opposite to the imaging surface, of the imaging device 29 shaped like a rectangle each side of which measures 1 mm or less and a set of plural linear conductors 55 which are exposed in the one end portion 57 and the other end portion 61 of the plate-like board 49 to be connected to the back surface 51 of the imaging device 29; an end surface contact step of bringing the one end surface 59 of the board 49 into contact with the back surface 51; a conductive material fixing step of electrically connecting the pads 53 and the conductors 55 via the low melting point conductive material 41 that has been melted by applying laser light to the low melting point conductive material 41 so that the temperature of the low melting point conductive material 41 becomes higher than its melting temperature; and a cable connecting step of joining the plural core wires 63 of the cable 25 to portions, exposed in the other end portion 61, of the plural conductors 55, respectively.

As described above, in this cable connection method of a camera module, laser light is used as a means for melting the low melting point conductive material 41 in the conductive material fixing step. Unlike in the case of blowing high-temperature air 73, laser light enables local, deep melting with a reduced amount of input heat while the illumination region is positioned with high accuracy. Thus, thermal stress on the imaging device 29 can be suppressed. Furthermore, the use of laser light makes it possible to control increase and decrease of the illumination area easily by defocusing the laser light by moving a condenser lens along the optical axis. This makes it possible to form a very small molten pool of the low melting point conductive material 41 with high accuracy.

A further cable connection method of a camera module includes a conductive material applying step of applying an unsolidified conductive material 41 to at least one of a set of plural pads 53 formed on the back surface 51, opposite to the imaging surface, of the imaging device 29 shaped like a rectangle each side of which measures 1 mm or less and a set of plural linear conductors 55 which are exposed in the one end portion 57 and the other end portion 61 of the plate-like board 49 to be connected to the back surface 51 of the imaging device 29; an end surface contact step of bringing the one end surface 59 of the board 49 into contact with the back surface 51; a conductive material fixing step of electrically connecting the pads 53 and the conductors 55 via the low melting point conductive material 41 that has been melted by heating the low melting point conductive material 41 in a reflow furnace; and a cable connecting step of joining the plural core wires 63 of the cable 25 to portions, exposed in the other end portion 61, of the plural conductors 55, respectively.

As described above, in this cable connection method of a camera module, the imaging device 29 and the board 49 in which cream solder is applied to the pads 53 and the conductors 55 in advance are heated in a reflow furnace. This makes it possible to braze the conductors 55 to the plural respective pads 53 at one time. In the camera module 45, thermal stress on the imaging device 29 can be suppressed by heating the one end portion 57 and the other portion 61 of the board 49 separately. In the camera module 45, it is possible to braze the imaging device 29 and the cable 25 to the board 49 at the same time as the above brazing by applying cream solder also to the core wires of the cable 25 and portions, exposed in the other portion 61, of the conductors 55 and making positioning between the former and the latter in advance.

Embodiment 2

Next, an endoscope system 11 according to a second embodiment and a camera 200 (e.g., endoscope) that is part of the endoscope system 11 will be described. In the second embodiment, members having the same ones in the first embodiment will be given the same symbols as the latter and will be described in a simplified manner or will not be described at all to avoid undue redundancy.

Figure 11:
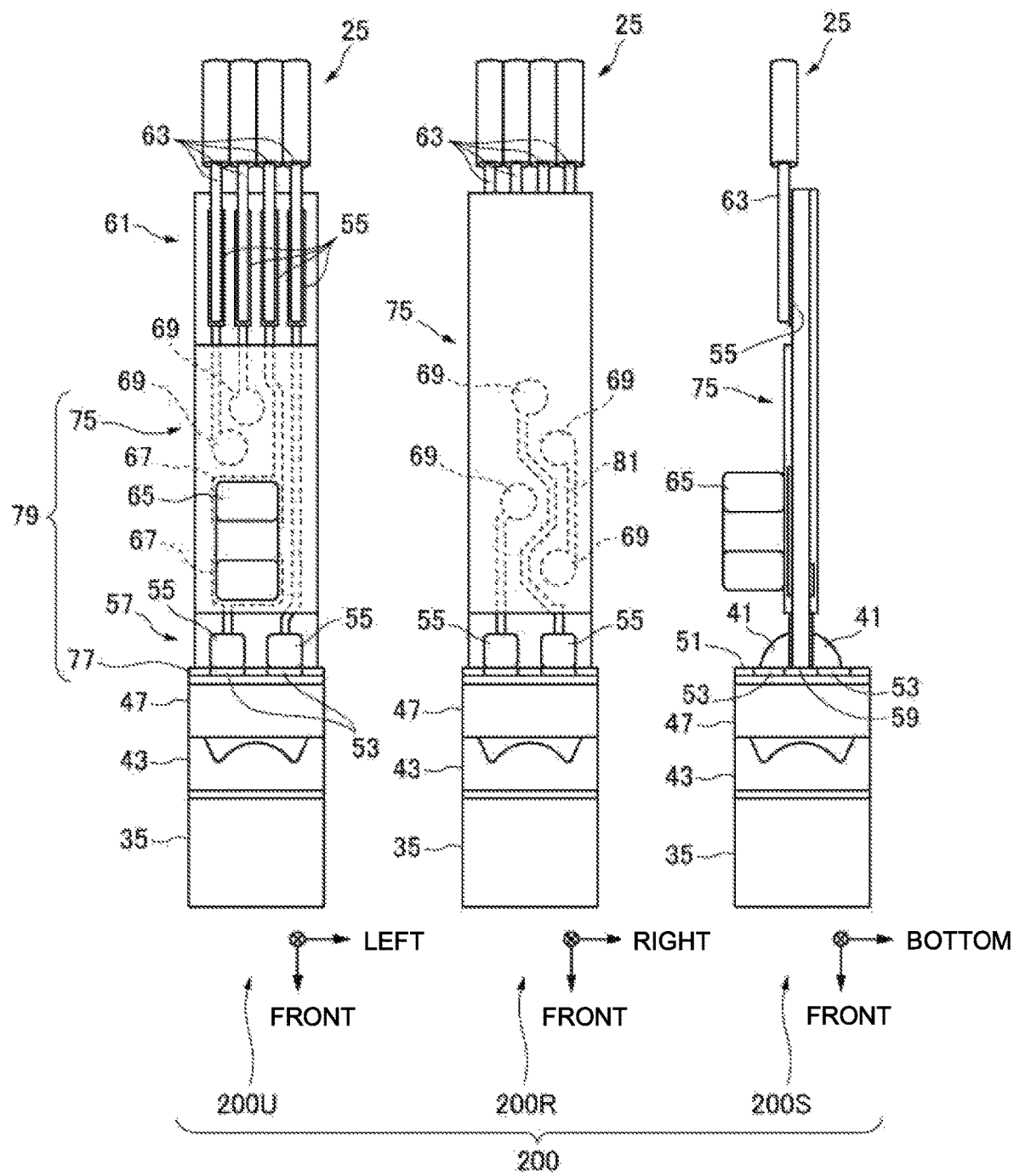
FIG. 11 is a plan view, a bottom view, and a side view of an essential part of a camera according to a second embodiment and illustrates its configuration.

FIG. 11 is a plan view, a bottom view, and a side view of an essential part of the camera 200 and shows its configuration. In FIG. 11, the plan view, the bottom view, and the side view of the camera 200 are denoted by 200U, 200R, and 200S, respectively. In FIG. 11, low melting point conductive materials 41 are omitted in the plan view 200U and the bottom view 200R.

In the camera 200, in one end portion 57 of a board 75, conductors 55 are exposed on the front surface and the back surface. In the second embodiment, an electric component 65 is mounted on the top surface of the board 75.

Figure 12:
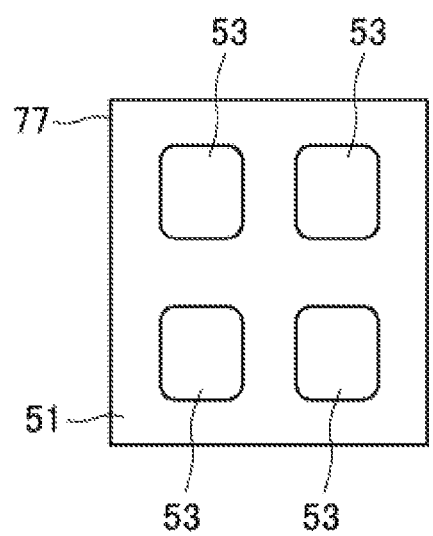
FIG. 12 is a rear view of an imaging device on which small rectangular pads are formed that are long in the thickness direction of a board.

FIG. 12 is a rear view of an imaging device 77 on which small rectangular pads 53 are formed that are long in the thickness direction of the board 75. In the camera 200, four pads 53 are formed on the back surface 51 of the imaging device 77. The four pads 53 are arranged close to the respective corners of the rectangular imaging device 77.

In the camera 200, the pads 53 which are provided in a camera module 79 is shaped like a circle, a square, or a rectangle.

The pads 53 shaped like a rectangle can be made higher in solder fixing strength than in the case where they are shaped like a circle.

Figure 13:
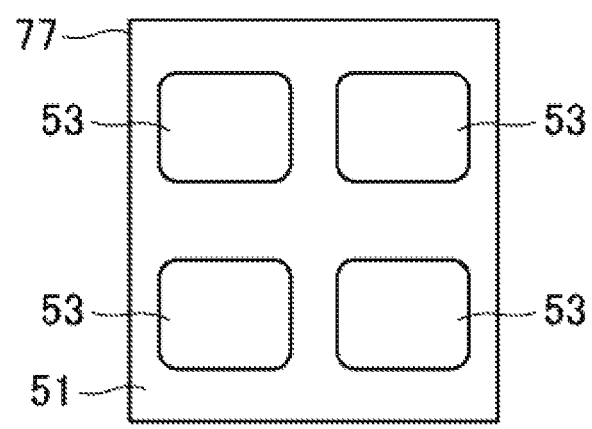
FIG. 13 is a rear view of an imaging device on which rectangular pads are formed that are long in the width direction of the board.

FIG. 13 is a rear view of an imaging device 77 on which rectangular pads 53 are formed that are long in the width direction of the board 75. Since the pads 53 are rectangular, their length in one direction is increased and the fixing strength in the desired direction can be made higher than in the directions other than the one direction.

Figure 14:
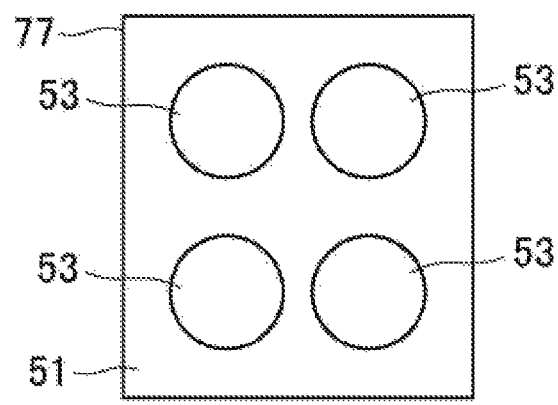
FIG. 14 is a rear view of an imaging device on which circular pads are formed.

FIG. 14 is a rear view of the imaging device 77 on which circular pads 53 are formed. Since the pads 53 are circular, the interference with adjacent pads is made weaker than in the case where they are rectangular, thereby the pads 53 can be arranged at high densities in the horizontal and vertical directions (e.g., staggered arrangement).

Figure 15:
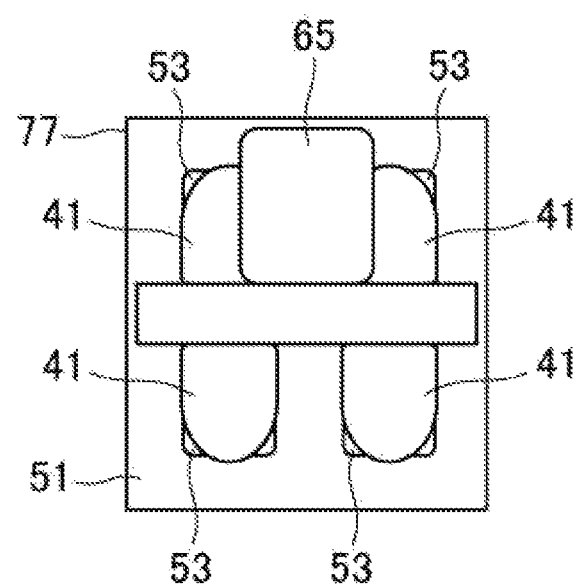
FIG. 15 is a rear view of the imaging device to whose pads shown in FIG. 12 the board is fixed.

FIG. 15 is a rear view of the imaging device 77 to whose pads 53 shown in FIG. 12 the board 75 is fixed. The two square pads 53 are formed on the back surface 51 of the imaging device 77 at the top-left and top-right positions. A pair of conductors 55 that are exposed in the one end portion 57 of the board 75 are electrically connected to these respective pads 53 by low melting point conductive materials 41. The two square pads 53 are formed on the back surface 51 of the imaging device 77 at the bottom-left and bottom-right positions. A pair of conductors 55 that are exposed in the bottom surface of the one end portion 57 of the board 75 are electrically connected to these respective pads 53 by low melting point conductive materials 41. The square pads 53 can suppress thermal stress on the imaging device 77 because the low melting point conductive materials 41 are fixed to the square pads 53 in small areas.

Figure 16:
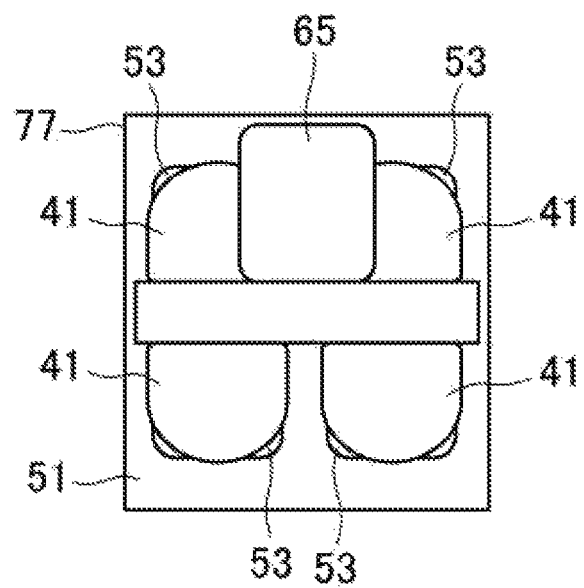
FIG. 16 is a rear view of the imaging device to whose pads shown in FIG. 13 the board is fixed.

FIG. 16 is a rear view of the imaging device 77 to whose pads 53 shown in FIG. 13 the board 75 is fixed. Where the imaging device 77 has the rectangular pads 53, larger low melting point conductive materials 41 can be fixed to them than in the case where the imaging device 77 has square pads 53. The rectangular pads 53 can increase the fixing strength of the imaging device 77 because the low melting point conductive materials 41 are fixed to the rectangular pads 53 in large areas.

Figure 17:
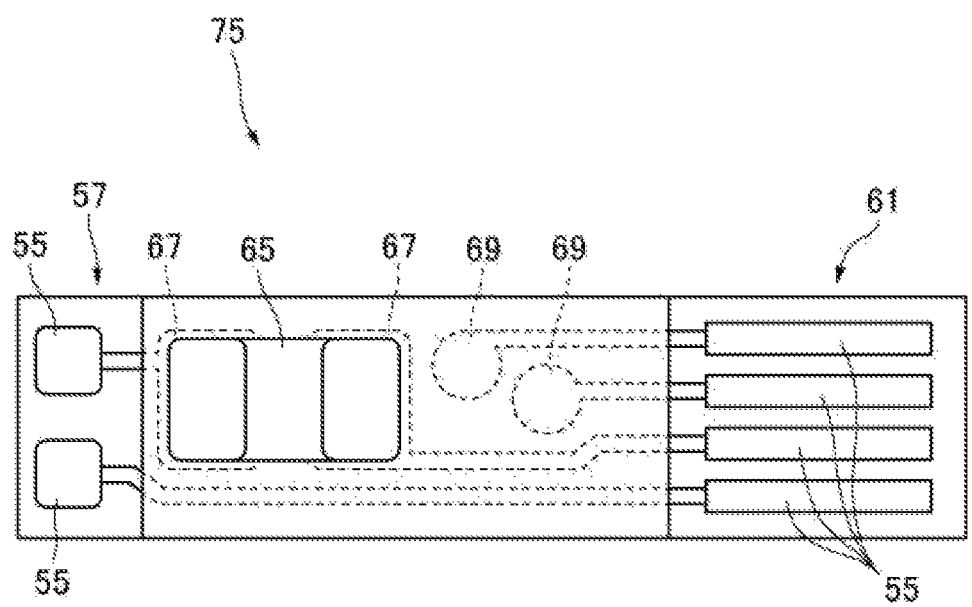
FIG. 17 is a plan view of the board shown in FIG. 11.

FIG. 17 is a plan view of the board 75 shown in FIG. 11. Four conductors 55 are exposed on the top surface of the other end portion 61 of the board 75. Among the four conductors 55, the two right-hand conductors 55 extend to the bottom surface through respective via holes 69. One of the two left-hand conductors 55 is exposed in the one end portion 57 and the other is connected to the rear land 67. The front land 67 is connected to a conductor 55 that is exposed in the one end portion 57. Thus, in the board 75, the two conductors 55 are exposed in the top surface of the one end portion 57.

Figure 18:
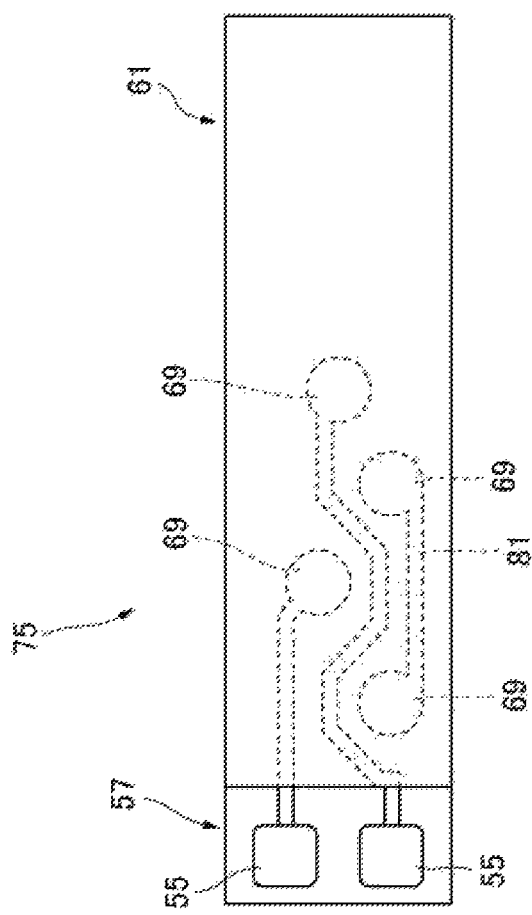
FIG. 18 is a bottom view of the board shown in FIG. 11.

FIG. 18 is a bottom view of the board 75 shown in FIG. 11. On the other hand, on the bottom surface of the board 75, two conductors 55 are exposed in the one end portion 57. Of these two conductors 55, the right-hand conductor 55 reaches one via hole 69 having an opening in the top surface. The other conductor 55 is connected to the rear land 67 formed on the top surface. One short conductor 81 is formed on the bottom surface of the board 75. The rear end of the short conductor 81 reaches the other via hole 69 having an opening in the top surface. The front end of the short conductor 81 is connected to the front land 67 formed on the top surface.

In this camera module 79, since the one end portion 57 of the board 75 is sandwiched between the pairs of low melting point conductive materials 41 from both of the front side and the back side, the strength of fixing of the imaging device 77 and the board 75 can be made higher than in the case where electrical connection is made only on one side.

The camera module 79 according to the second embodiment can also realize mass production and reduce the manufacturing cost by making it possible to attain positioning between the pads 53 and conductors 55 without requiring skills and to thereby enable automatic assembling easily.

Embodiment 3

Next, an endoscope system 11 according to a third embodiment and a camera 300 (e.g., endoscope) that is part of the endoscope system 11 will be described. In the third embodiment, members having the same ones in the first embodiment will be given the same symbols as the latter and will be described in a simplified manner or will not be described at all to avoid undue redundancy.

Figure 19:
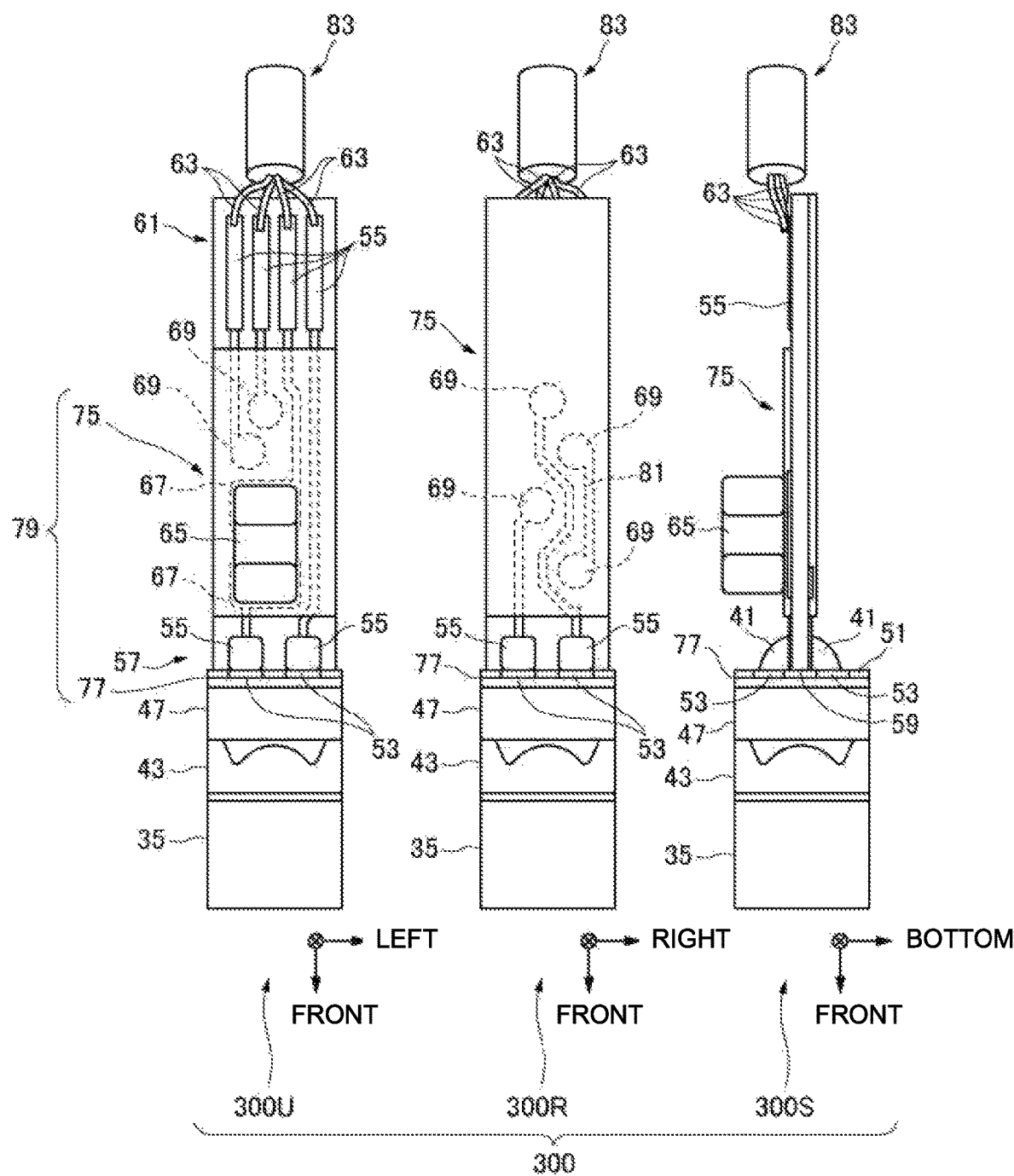
FIG. 19 is a plan view, a bottom view, and a side view of an essential part of a camera according to a third embodiment and illustrates its configuration.

FIG. 19 is a plan view, a bottom view, and a side view of an essential part of the camera 300 and shows its configuration. In FIG. 19, the plan view, the bottom view, and the side view of the camera 300 are denoted by 300U, 300R, and 300S, respectively. In FIG. 19, low melting point conductive materials 41 are omitted in the plan view 300U and the bottom view 300R.

The same camera module 79 as employed in the second embodiment is employed in this camera 300. On the other hand, a cable 83 is employed which bundles plural core wires 63 and has a round shape. In the cable 83, each core wire 63 is covered with an insulating covering. A conductor 55 in an end portion, exposed by removing the insulating covering there, of each core wire 63 is connected to the associated conductor 55 in the other end portion 61 of the board 75. In this manner, a common round cable 83 may be employed in the camera 300.

The camera module 79 according to the third embodiment can also realize mass production and reduce the manufacturing cost by making it possible to attain positioning between the pads 53 and conductors 55 without requiring skills and to thereby enable automatic assembling easily.

Although the various embodiments have been described above with reference to the drawings, it goes without saying that the disclosure is not limited to those examples. It is apparent that those skilled in the art could conceive various changes, modifications, replacements, additions, deletions, or equivalents within the confines of the claims, and they are naturally construed as being included in the technical scope of the disclosure. Constituent elements of the above-described embodiments may be combined in a desired manner without departing from the spirit and scope of the invention.

The present application is based on Japanese Patent Application No. 2018-074004 filed on Apr. 6, 2018, the disclosure of which is incorporated herein by reference.

Industrial Applicability

The present disclosure is useful to provide camera modules, cameras, and cable connection methods of a cameral module capable of realizing mass production and reducing the manufacturing cost by making it possible to attain positioning between pads and conductors without requiring skills and to thereby enable automatic assembling easily.

REFERENCE SIGNS LIST

25: Cable
29: Imaging device
41: Low melting point conductive material
43: Lens
45: Camera module
49: Board
51: Back surface
53: Pad
55: Conductor
57: One end portion
59: One end surface
61: The other end portion
63: Core wire
65: Electric component
73: High-temperature air
75: Board
79: Camera module
100, 200, 300: Camera

The invention claimed is:

1. A camera module, comprising:
an imaging device which is rectangular and is provided with four pads on a back surface that is opposite to an imaging surface, the four pads being arranged in a same plane;
a board which is formed with a rectangular plate on which four linear conductors are arranged and which is covered with an insulating coating or an insulation layer, with sides of the board, which are located at ends in an extension direction of the four linear conductors, of one end portion and the other end portion of the rectangular plate being shorter than each side of the imaging device, and the four linear conductors being exposed in the one end portion and the other end portion on a front plate surface of the rectangular plate; and
conductive materials which connect, to the four pads, the exposed portions of the four linear conductors in the one end portion, respectively, with one end surface of the board being in contact with the back surface,
wherein the four linear conductors are arranged parallel with each other in the same plane and are partially covered with the insulating coating or the insulating layer,
in the other end portion, the four linear conductors are exposed on the front plate surface,
the four linear conductors are connected to the four pads, via the conductive materials, in a direction perpendicular to the same plane,
among the four linear conductors, two linear conductors extend to a back plate surface of the board via respective through-holes in the board, and
the board includes two lands for mounting of an electric component, the two lands being on the back plate surface of the board and connected to the two linear conductors via the respective through-holes.

2. The camera module according to claim 1, wherein plural core wires of a cable are connected to portions, exposed in the other end portion of the board, of the four linear conductors, respectively.

3. The camera module according to claim 2, wherein each of the plural core wires is insulated and covered with an internal covering of the cable, each of the plural core wires further being covered with a shield covering outside the internal covering.

4. The camera module according to claim 1, wherein an electric component is mounted on the board so as to be electrically connected to the four linear conductors.

5. The camera module according to claim 1, wherein each of the four pads is shaped like a circle, a square, or a rectangle.

6. A camera comprising:
a camera module according to claim 1; and
a lens disposed on the imaging surface of the imaging device.

7. The camera module according to claim 1, wherein each side of the imaging device measures 1 mm or less.

8. A cable connection method of a camera module for connecting a cable to the camera module, the camera module including an imaging device, the cable connection method comprising:
applying an unsolidified conductive material to at least one of four pads formed on a back surface, opposite to an imaging surface, of the imaging device and four linear conductors, the four pads being arranged in a same plane, the four linear conductors being arranged parallel with each other in the same plane, the four linear conductors being exposed in one end portion and the other end portion on a front plate surface of a plate-like board to be connected to the back surface of the imaging device;
bringing one end surface of the board into contact with the back surface;
electrically connecting the four pads and the four linear conductors via the conductive material that has been melted by blowing, over the conductive material, high-temperature air whose temperature is higher than a melting temperature of the conductive material; and
joining plural core wires of the cable to portions, exposed in the other end portion, of the four linear conductors, respectively,
wherein, in the electrically connecting, the four linear conductors are connected to the four pads, via the conductive materials, in a direction perpendicular to the same plane,
among the four linear conductors, two linear conductors extend to a back plate surface of the board via respective through-holes in the plate-like board, and
the plate-like board includes two lands for mounting of an electric component, the two lands being on the back plate surface of the plate-like board and connected to the two linear conductors via the respective through-holes.

9. A cable connection method of a camera module for connecting a cable to the camera module, the camera module including an imaging device, the cable connection method comprising:
applying an unsolidified conductive material to at least one of a set of four pads formed on a back surface, opposite to an imaging surface, of the imaging device and a set of four linear conductors, the four pads being arranged in a same plane, the four linear conductors being arranged parallel with each other in the same plane, the four linear conductors being exposed in one end portion and the other end portion on a front plate surface of a plate-like board to be connected the back surface of the imaging device;
bringing one end surface of the board into contact with the back surface;
electrically connecting the four pads and the four linear conductors via the conductive material that has been melted by applying laser light to the conductive material so that the temperature of the conductive material becomes higher than its melting temperature; and
joining plural core wires of the cable to portions, exposed in the other end portion, of the four linear conductors, respectively,
wherein, in the electrically connecting, the four linear conductors are connected to the four pads, via the conductive materials, in a direction perpendicular to the same plane,
among the four linear conductors, two linear conductors extend to a back plate surface of the board via respective through-holes in the plate-like board, and
the plate-like board includes two lands for mounting of an electric component, the two lands being on the back plate surface of the plate-like board and connected to the two linear conductors via the respective through-holes.

10. A cable connection method of a camera module for connecting a cable to the camera module, the camera module including an imaging device, the cable connection method comprising:
applying an unsolidified conductive material to at least one of a set of four pads formed on a back surface, opposite to an imaging surface, of the imaging device and a set of four linear conductors, the four pads being arranged in a same plane, the four linear conductors being arranged parallel with each other in the same plane, the four linear conductors being exposed in one end portion and the other end portion on a front plate surface of a plate-like board to be connected to the back surface of the imaging device;
bringing one end surface of the board into contact with the back surface;
electrically connecting the four pads and the four linear conductors via the conductive material that has been melted by heating the conductive material in a reflow furnace; and
joining plural core wires of the cable to portions, exposed in the other end portion, of the four linear conductors, respectively,
wherein, in the electrically connecting, the four linear conductors are connected to the four pads, via the conductive materials, in a direction perpendicular to the same plane,
among the four linear conductors, two linear conductors extend to a back plate surface of the board via respective through-holes in the plate-like board, and
the plate-like board includes two lands for mounting of an electric component, the two lands being on the back plate surface of the plate-like board and connected to the two linear conductors via the respective through-holes.

11. The cable connection method of the camera module according to claim 8, wherein the imaging device is formed in a rectangle shape, and each side of the imaging device is 1 mm or less.

12. The cable connection method of the camera module according to claim 9, wherein the imaging device is formed in a rectangle shape, and each side of the imaging device is 1 mm or less.

13. The cable connection method of the camera module according to claim 10, wherein the imaging device is formed in a rectangle shape, and each side of the imaging device is 1 mm or less.

14. The camera module according to claim 1, wherein the four linear conductors are fixed to the four pads via the conductive materials.

15. The camera module according to claim 1, wherein the conductive materials include melted materials, with the four linear conductors being fixed to the four pads via the melted materials.

16. The camera module according to claim 1, wherein the melted materials include low melting point conductive materials.

17. The camera module according to claim 1, wherein each of the four pads has a same length as each side of the imaging device.

18. The camera module according to claim 1, wherein the four pads are arranged at regular intervals in a direction perpendicular to sides of the imaging device.

\* \* \* \* \*